US007629286B2

(12) United States Patent
Haddad et al.

(10) Patent No.: US 7,629,286 B2
(45) Date of Patent: Dec. 8, 2009

(54) PHOSPHORUS ADDITION PROCESS FOR IMPROVEMENT OF CATALYSTS SUITABLE FOR MALEIC ANHYDRIDE PRODUCTION

(75) Inventors: Muin S. Haddad, Naperville, IL (US); Gary V. Goeden, Batavia, IL (US)

(73) Assignee: INEOS USA LLC, Lisle, IL (US)

( * ) Notice: Subject to any disclaimer, the term of this patent is extended or adjusted under 35 U.S.C. 154(b) by 222 days.

(21) Appl. No.: 11/415,045

(22) Filed: May 1, 2006

(65) Prior Publication Data

US 2006/0247447 A1    Nov. 2, 2006

(51) Int. Cl.
*B01J 27/00* (2006.01)
*B01J 27/198* (2006.01)
*B01J 27/188* (2006.01)
*B01J 27/19* (2006.01)
*B01J 27/192* (2006.01)
*C07D 307/34* (2006.01)

(52) U.S. Cl. ............... 502/208; 502/209; 502/210; 502/211; 502/212; 549/259; 549/260

(58) Field of Classification Search ......... 502/208–212; 549/259, 260
See application file for complete search history.

(56) References Cited

U.S. PATENT DOCUMENTS

| | | | | | |
|---|---|---|---|---|---|
| 3,296,282 | A | * | 1/1967 | Kerr | 549/259 |
| 4,515,899 | A | * | 5/1985 | Click et al. | 502/35 |
| 4,515,904 | A | * | 5/1985 | Edwards | 502/209 |
| 4,596,878 | A | * | 6/1986 | Click et al. | 549/259 |
| 4,647,673 | A | * | 3/1987 | Bremer et al. | 549/260 |
| 4,701,433 | A | * | 10/1987 | Edwards | 502/209 |
| 4,780,548 | A | * | 10/1988 | Edwards et al. | 549/259 |
| 4,950,769 | A | * | 8/1990 | McCandless et al. | 549/257 |
| 4,996,179 | A | * | 2/1991 | Haddad et al. | 502/209 |
| 5,011,945 | A | | 4/1991 | Taheri | |
| 5,095,125 | A | * | 3/1992 | Haddad et al. | 549/259 |
| 5,117,007 | A | * | 5/1992 | Taheri | 549/259 |
| 5,185,455 | A | * | 2/1993 | Ebner | 549/259 |
| 5,506,187 | A | * | 4/1996 | Haddad et al. | 502/209 |
| 6,300,505 | B1 | * | 10/2001 | Burnett et al. | 549/259 |
| 7,060,649 | B2 | * | 6/2006 | Weiguny et al. | 502/209 |

FOREIGN PATENT DOCUMENTS

| | | | |
|---|---|---|---|
| EP | 0 123 467 | | 4/1983 |
| EP | 123467 A1 | * | 10/1984 |
| GB | 1 464 198 | | 8/1975 |
| JP | 50 010714 | | 4/1975 |
| WO | 2006/199257 | * | 11/2006 |

OTHER PUBLICATIONS

Search Report for PCT/US2006/016750.*

* cited by examiner

*Primary Examiner*—Patricia L Hailey
(74) *Attorney, Agent, or Firm*—David P. Yusko; James J. Drake; Vik Panchal

(57) ABSTRACT

A process is disclosed for the improvement of fluid bed vanadium phosphorus mixed oxide catalyst performance in the manufacture of maleic anhydride from butane, which process comprises impregnating the VPO catalyst powder with a phosphorus compound, such as an alkyl ester of orthophosphoric acid and then using this impregnated catalyst powder to provide phosphorus to the maleic anhydride producing catalyst.

34 Claims, No Drawings

PHOSPHORUS ADDITION PROCESS FOR IMPROVEMENT OF CATALYSTS SUITABLE FOR MALEIC ANHYDRIDE PRODUCTION

BACKGROUND OF THE INVENTION

The present invention relates to a fluid bed process for the production of maleic acid or maleic anhydride from 4-carbon hydrocarbons using a vanadium phosphorus oxide (VPO) catalyst wherein phosphorus loss from the catalyst, which occurs during the course of the reaction, is replaced by impregnating VPO catalyst with alkyl ester of orthophosphoric acid, such as triethylphosphate (TEP) and adding the alkyl ester-impregnated catalyst to the fluid catalyst bed, thereby improving catalyst performance.

Large quantities of maleic an hydride are produced each year throughout the world, since maleic anhydride can be employed as a versatile intermediate for chemical synthesis and is often used in the production of alkyl resins. Maleic acid is a precursor to maleic anhydride and can also be used as the starting material for the production of 1,4-butanediol (BDO).

Maleic anhydride may be produced by vapor phase oxidation of n-butane in air using a fixed bed or fluid bed vanadium phosphorus oxide (VPO) catalyst.

The advantages of fluid bed hydrocarbon oxidation processes compared to fixed bed hydrocarbon oxidation processes are well known in the art, including the improvement of temperature control and heat transfer for oxidation reactions.

Catalysts containing vanadium and phosphorus oxides have been used in the oxidation of 4-carbon atom hydrocarbons, such as n-butane, n-butenes, 1,3-butadiene or mixtures thereof with molecular oxygen or oxygen-containing gas to produce maleic anhydride. Conventional methods of preparing these catalysts involve reducing a pentavalent vanadium compound, and combining the same with a phosphorus compound, and if desired, promoter element compounds under conditions which will provide vanadium in a valence state below +5 to form catalyst precursors capable of being converted to vanadium phosphorus oxide. The catalyst oxide precursor is then recovered and converted to active catalytic material before or after the suitable catalyst particles for either fixed bed or fluid bed are formed.

U.S. Pat. Nos. 3,888,886; 3,905,914; 3,931,046; 3,932,305 and 3,975,300 disclose the testing of promoted vanadium phosphorus oxide catalysts for maleic anhydride production from butane in one inch diameter fluid bed reactors. In most instances, the catalysts were prepared by forming the catalyst precursor in aqueous media (in U.S. Pat. No. 3,975,300 the precursor was formed in a paste of a vanadium compound, a phosphorus compound and an organic reducing agent), drying and thereafter grinding and sieving the precursor to a powder of about 74 to 250 microns size. This manner of preparation, however, does not obtain the attrition resistant catalyst particles preferred for successful fluid bed operation.

Commercial fluid bed catalysts are preferably microspheroidal particles within the range of about 20 to about 300 microns in average diameter, preferably having about 80% of the particles within the range of about 30 to about 80 microns in diameter. Most preferably, about 25 to about 40% of the particles have an average diameter of less than 45 microns.

U.S. Pat. No. 4,647,673, incorporated herein by reference in its entirety, discloses a process for the preparation of attrition resistant, microspheroidal fluid bed catalysts comprising the mixed oxides of vanadium and phosphorus in which a vanadium phosphorus mixed oxide catalyst precursor is densified, comminuted, formed into fluidizable particles and calcined under fluidization-type conditions.

As in other vanadium phosphate catalysts used for either fluid bed or fixed bed butane oxidation, phosphorus loss occurs with catalyst use. This loss may lead to a reduction of the catalyst's maleic anhydride yield. This loss is deleterious to plant capacity and economics of production. Therefore, methods of phosphorus addition have been developed to compensate for this phosphorus loss and hence recover part or all of the yield lost. Continuous addition of phosphorus also has the added advantage of maintaining the maleic anhydride yield at an economical and stable level.

United Kingdom Patent Specification 1,464,198 discloses the reactivation or regeneration of certain vanadium-phosphorus-oxygen catalyst complexes promoted with zirconium, hafnium, chromium, iron, lanthanum, or cerium by having the catalyst contacted during vapor-phase oxidation with an alkyl ester of orthophosphoric acid having the formula $(RO)_3P{=}O$ wherein R is hydrogen or $C_1$ to $C_4$ alkyl, at least one R being $C_1$ to $C_4$ alkyl.

In U.S. Pat. No. 4,701,433, Edwards discloses a process for the manufacture of maleic anhydride from butane in the presence of a vanadium-phosphorus-oxygen catalyst or a vanadium-phosphorus-oxygen-co-metal catalyst, wherein water and a phosphorus compound are added to the reaction system to reversibly deactivate a portion of the catalyst in the catalyst bed containing a reaction exotherm (hot spot) prior to the addition of the phosphorus compound, which addition of phosphorus compound moves the reaction exotherm downstream into the catalyst bed, and an improved catalyst bed is obtained when the partially deactivated catalyst in the original "hot spot" location reactivates to produce a more isothermal catalyst bed.

Although Edwards, et al. recognized the utility of a more isothermal catalyst bed to improve yield, Edwards accomplished a more isothermal catalyst bed temperature by shifting the location of the original "hot spot" to a new location and then reactivating the old location. Edwards teaches that improvement in yield can be obtained as long as there is sufficient catalyst bed into which the exotherm may migrate. Edwards failed to recognize that constant shifting of the exotherm is inherently unstable and not suitable for long-term operation.

U.S. Pat. No. 4,780,548, Edwards, et al. teaches a continuous process for the vapor-phase oxidation of a n-butane feedstock to form maleic anhydride in which n-butane is contacted in the presence of molecular oxygen or air at an hourly space velocity of about 100 to about 4000 cubic centimeters of feed per cubic centimeter of catalyst per hour with a vanadium-phosphorus-oxygen catalyst wherein the catalyst is regenerated continuously or batchwise by contacting it during the vapor phase oxidation with an alkyl ester of orthophosphoric acid having the formula $(RO)_3P{=}O$ wherein R is hydrogen or $C_1$ to $C_4$ alkyl, at least one R being $C_1$ to $C_4$ alkyl, wherein the amount of water added is about 1000 parts per million to about 40,000 parts per million by weight of the reactor feed gas stream and the amount of the alkyl ester added is about 0.1 parts per million to about 100,000 parts per million by weight of the reactor feed gas stream. The gaseous feed stream to the reactor will contain from about 0.2 to about 1.7 mole % of n-butane but about 0.8 to about 1.5 mole % of n-butane is satisfactory for optimum yield from the process of the invention. Edwards teaches that higher concentrations can be employed but explosive hazards may be encountered. Even though Edwards acknowledged that explosive mixtures could be employed, above 1.5-1.7 moles n-butanes, Edwards did not recognize that an isothermal reaction employing a higher concentration of n-butane would result in a yield continuously maintained at a high level for extended periods of time despite the possibility of explosive hazards.

Becker, et al., U.S. Pat. No. 4,795,818 disclosed a method for optimizing the yield of a vanadium-phosphorus catalyst during the oxidation of n-butane to maleic anhydride, wherein a volatile phosphorus compound is continuously added at a rate selected to maintain maximum yield while holding the operating temperature constant, the operating temperature being monitored preferably by the outlet gas temperature. Becker et al., indicate that the amount of phosphorus compound to be added should be sufficient to prevent decline in operating temperature. Becker, et al., fail to recognize the impact of the water added to the reaction and rely only on the addition of a volatile phosphorus compound to the process.

In U.S. Pat. No. 4,515,899, Click, et al., teach that the useful life of a vanadium-phosphorus-oxygen catalyst can be extended in fixed bed reactors by treatment with a phosphorus compound followed by steam treatment and furnish data showing movement of the exotherm further into the catalyst bed.

U.S. Pat. No. 5,117,007, incorporated herein by reference in its entirety, discloses a continuous process for the production of maleic anhydride by the partial oxidation of a hydrocarbon feedstock comprising n-butane in a concentration of at least 1.6 mole percent wherein a mixture of the feedstock and an oxidizing medium is contacted with a vanadium-phosphorus-oxygen catalyst wherein a solution of water and an alkyl ester of orthophosphoric acid is continually added to the feedstock, wherein the ratio of water to elemental phosphorus in said alkyl ester is in the range of from about 6500:1 wt. to about 50,000:1 wt., water to phosphorus, and the differences in reaction temperature throughout the entire reaction zone is less than about 45° C. (80° F.).

In the partial oxidation of n-butane to maleic anhydride, the reaction is highly exothermic and a catalyst hot spot temperature can develop with potential of a runaway oxidation reaction and consequent complete loss of product yield. Such a development of a hot spot temperature in a fixed bed reactor is potentially extremely detrimental to the progress of the oxidation reaction. The hot spot temperature readily occurs in the oxidation and is quite sensitive to variations in the concentration of feed hydrocarbon. Small increases in the concentration of the hydrocarbon feed can result in large increases in hot spot temperature and a concurrent decrease in selectivity and yield. In addition, high hot spot temperatures can shorten the useful life of the catalyst being employed. It is therefore necessary to avoid the development of an excessively high hot spot temperature and to maintain an isothermal catalyst temperature range over the entire length of the reaction zone to obtain consistent high yield and lengthened catalyst life. Also, consistent high product yield requires a process with consistent process parameters.

U.S. Pat. No. 5,117,007 discloses that the beneficial effect of adding a phosphorus compound in water, in certain ratios to each other, to control the reaction temperature profile in oxidation of n-butane to maleic anhydride can be obtained over the entire reaction zone of a fixed bed reactor. The beneficial effect occurs over the entire reaction zone including the so-called hot spot temperature zone but also a significant beneficial effect of the reaction temperature profile has been found to result despite operation in the flammability zone which exists wherein concentration of n-butane in the feed is about 1.7 mole %, or higher, and air is the source of oxygen. The required ratio of water to phosphorus in the phosphorus compound relates to the concentration of n-butane, and also to the reactor size and shape. An isothermal reaction zone temperature thereby results wherein the reaction zone temperature gradient is within a maximum range of about 45° C. (80° F.) with consequent increase in overall yield.

As discussed above, one method of phosphorus addition technology is based on adding phosphorus, in the vapor phase, to a fixed bed catalysts or a fluid bed catalyst. In one method of phosphorous addition, for example, phosphorus, in the form of triethylphosphate (TEP), is added in the vapor phase. This technology has provided the beneficial effect of stabilizing and preventing loss of catalyst yield; however, an undesirable effect of adding phosphorus to a VPO fluid bed catalyst used to oxidize butane to make maleic acid or maleic anhydride has been an increase in operating temperature. This high temperature causes undesirable effects, such as limiting the throughput to the reactor and also accelerating degradation of catalyst physical properties such as surface area and pore volume, which are important parameters for good catalyst performance. Therefore, there is a need to find a way to add phosphorus to the butane oxidation reaction to increase maleic anhydride yield without causing an increase in the operating temperature which will harm the catalyst.

We discovered that by impregnating a VPO catalyst with an alkyl ester of an orthophosphate such as triethylphosphate (TEP), the TEP-impregnated VPO catalyst could be used for adding phosphorus to the fluid bed butane oxidation reaction, and thereby achieving the desired increase in maleic anhydride yield at a lower operating temperature and, in addition, at a significantly lower concentration of TEP when compared to the to the vapor phase TEP addition mode.

Thus, the present invention has the advantages of permitting the addition of phosphorus without causing temperature increases which can harm the catalyst and also enabling one to use less TEP to replace lost phosphorus, which provides an economic benefit.

SUMMARY OF THE INVENTION

The present invention relates to a fluid bed process for the production of maleic anhydride by the oxidation of a feed comprising $C_4$ hydrocarbons with molecular oxygen or an oxygen containing gas in a fluid bed reactor at a reactor temperature of about 325° C. to about 500° C. in the presence of an attrition resistant, fluidizable microspheroidal catalyst containing the mixed oxides of vanadium and phosphorus, wherein the catalyst is prepared by:

(a) preparing a vanadium phosphorus mixed oxide containing catalyst precursor;

(b) densifying the catalyst precursor;

(c) comminuting the catalyst precursor to an average particle size less than about one micron in diameter;

(d) forming fluidizable particles having a bulk density greater than or equal to 0.75 grams per cubic centimeter from the densified, comminuted catalyst precursor; and (e) calcining the fluidizable particles under fluidization-type conditions, wherein the catalyst performance is improved by the addition of catalyst containing an alkyl ester of orthophosphoric acid having the formula $(RO)_3P=O$ wherein R is hydrogen or $C_1$ to $C_4$ alkyl, at least one R being $C_1$ to $C_4$ alkyl in an amount sufficient to provide from about 0.000002 to about 1.0 pounds of alkyl ester of orthophosphoric acid per 100 pounds of total catalyst bed per day.

The present invention also relates to a fluid bed process for the production of maleic anhydride by the oxidation of a feed comprising $C_4$ hydrocarbons with molecular oxygen or an oxygen containing gas in a fluid bed reactor at a reactor temperature of about 325° C. to about 500° C. in the presence of an attrition resistant, fluidizable microspheroidal catalyst containing the mixed oxides of vanadium and phosphorus, wherein the catalyst is prepared by:

(a) preparing a vanadium phosphorus mixed oxide containing catalyst precursor;

(b) densifying the catalyst precursor;

(c) comminuting the catalyst precursor to an average particle size less than about one micron in diameter;

(d) forming fluidizable particles having a bulk density greater than or equal to 0.75 grams per cubic centimeter from the densified, comminuted catalyst precursor; and (e) calcining the fluidizable particles under fluidization-type conditions, wherein the catalyst performance is improved by the addition of fluidizable catalyst containing about 1 to about 25 parts by weight of an alkyl ester of orthophosphoric acid having the formula $(RO)_3P=O$, wherein R is hydrogen or $C_1$ to $C_4$ alkyl, at least one R being $C_1$ to $C_4$ alkyl, per 100 parts by weight catalyst.

Preferred alkyl esters of orthophosphoric acid are triethylphosphate and trimethylphosphate.

In the present invention, a fluid bed VPO catalyst is mixed with an alkyl ester of orthophosphoric acid, such as triethylphosphate, and the alkyl ester of orthophosphoric acid is absorbed into the pores of the catalyst so that the catalyst becomes impregnated with the alkyl ester of orthophosphoric acid. When the TEP-impregnated catalyst is added to the fluid bed reactor, the alkyl ester of orthophosphoric acid is released and provides phosphorus to improve catalyst performance. The catalyst which is impregnated with an alkyl ester of orthophosphoric acid may be added to the reactor alone or it can be mixed with catalyst which has not been impregnated with an alkyl ester of orthophosphoric acid to provide a fluidizable catalyst mixture capable of supplying the desired amount of the alkyl ester of orthophosphoric acid to the reaction.

The present invention also relates to an attrition resistant, fluidizable microspheroidal catalyst containing the mixed oxides of vanadium and phosphorus, wherein the catalyst is prepared by:

(a) preparing a vanadium phosphorus mixed oxide containing catalyst precursor;

(b) densifying the catalyst precursor;

(c) comminuting the catalyst precursor to an average particle size less than about one micron in diameter;

(d) forming fluidizable particles having a bulk density greater than or equal to 0.75 grams per cubic centimeter from the densified, comminuted catalyst precursor;

(e) calcining the fluidizable particles under fluidization-type conditions; and (f) mixing the fluidizable catalyst obtained in (e) with an alkyl ester of orthophosphoric acid having the formula $(RO)_3P=O$ wherein R is hydrogen or $C_1$ to $C_4$ alkyl, at least one R being $C_1$ to $C_4$ alkyl, to provide fluidizable catalyst containing from about 1 to about 25 parts by weight of the alkyl ester of orthophosphoric acid per 100 parts by weight catalyst, preferably about 7 to about 23 parts by weight of the alkyl ester of orthophosphoric acid per 100 parts by weight catalyst; more preferably about 8 to about 21 parts by weight of the alkyl ester of orthophosphoric acid per 100 parts by weight catalyst, and more preferably about 16 to about 19 parts by weight of the alkyl ester of orthophosphoric acid per 100 parts by weight catalyst.

Preferred alkyl esters of orthophosphoric acid are triethylphosphate and trimethylphosphate.

The present invention further relates to an attrition resistant, fluidizable miscrospheroidal catalyst containing the mixed oxides of vanadium and phosphorus, wherein the catalyst is prepared by:

(a) preparing a vanadium phosphorus mixed oxide containing catalyst precursor;

(b) densifying the catalyst precursor;

(c) comminuting the catalyst precursor to an average particle size less than about one micron in diameter;

(d) forming fluidizable particles having a bulk density greater than or equal to 0.75 grams per cubic centimeter from the densified, comminuted catalyst precursor;

(e) calcining the fluidizable particles under fluidization-type conditions; and (f) mixing the fluidizable catalyst obtained in (e) with triethylphosphate to provide fluidizable catalyst containing from about 1 to about 25 parts by weight of triethylphosphate per 100 parts by weight catalyst, preferably from about 7 to about 23 parts by weight of triethylphosphate per 100 parts by weight catalyst; more preferably about 8 to about 21 parts by weight of triethylphosphate per 100 parts by weight catalyst, and more preferably about 16 to about 19 parts by weight of triethylphosphate per 100 parts by weight catalyst.

DESCRIPTION OF THE PREFERRED EMBODIMENT(S)

The present invention relates to a fluid bed process for the production of maleic acid or maleic anhydride from 4-carbon hydrocarbons using a vanadium phosphorus oxide (VPO) catalyst wherein phosphorus lost from the catalyst, which occurs during the course of the reaction, is replaced by impregnating VPO catalyst with an alkyl ester of orthophosphoric acid having the formula $(RO)_3P=O$ wherein R is hydrogen or $C_1$ to $C_4$ alkyl, at least one R being $C_1$ to $C_4$ alkyl, such as triethylphosphate (TEP) and adding the TEP-impregnated catalyst to the fluid catalyst bed. This improves catalyst performance and provides an increase in maleic anhydride yield at lower operating temperatures.

Earlier methods of adding phosphorus involved using an on-line addition process whereby triethylphosphate (TEP) is added in the vapor phase; however, this can cause an undesirable increase in operating temperature. Because of this, it became clear that an alternative phosphorus addition that would result in the same yield improvement as TEP addition, but does not result in the same increase in operating temperature is needed We discovered that make-up catalyst enriched with an alkyl ester of orthophosphoric acid, such as TEP, could be used as a means of introducing the needed phosphorus for yield improvement without causing an undesirable increase in operating temperature.

Maleic anhydride is produced by vapor phase oxidation of n-butane in air using a fluid bed vanadium-phosphorus-oxygen (VPO) catalyst. As in other vanadium phosphate catalysts used for either fluid bed or fixed bed butane oxidation, phosphorus loss occurs with catalyst use. This loss may lead to a reduction of the catalyst's maleic anhydride yield. This loss is deleterious to plant capacity and economics of production. Therefore, methods of phosphorus addition have been developed to compensate for this phosphorus loss and hence recover part or all of the yield lost. Continuous addition of phosphorus also has the added advantage of maintaining the maleic anhydride yield at an economical and stable level.

A phosphorus addition technology based on adding triethylphosphate (TEP) in the vapor phase to fixed bed catalysts or to fluid bed catalysts has been used to compensate for phosphorus loss. This technology has been very effective in achieving the intended beneficial effect of stabilizing and preventing loss of catalyst yield in the fluid bed maleic anhydride process; however, undesired, outcome of adding phosphorus to the fluid bed VPO catalyst has been an increase in operating temperature. This high temperature has some negative effects, like limiting the throughput to the reactor and also accelerating degradation of catalyst physical properties like surface area and pore volume, which are important parameters for good catalyst performance.

It has been discovered that by impregnating the VPO catalyst with an alkyl ester of orthophosphoric acid and adding the impregnated catalyst to the fluid bed VPO catalyst periodically it is possible to add phosphorous to the VPO fluid bed catalyst and to achieve an increase in maleic anhydride yield at a lower operating temperature. An additional advantage is that significantly less of the alkyl ester of orthophosphate is needed than when the alkyl ester of orthophosphoric acid is added in the vapor phase as was the earlier practice. When a VPO catalyst is mixed with an alkyl ester of phosphoric acid, such as TEP, the liquid TEP is absorbed in the pores of the catalyst. When the catalyst is added to the fluid bed reactor via the catalyst addition pipe, the TEP is volatilized and released to the process, and it improves catalyst performance by replacing phosphorus leading to improved maleic anhydride yields and lower process temperature.

The preferred alkyl phosphate compound is an alkyl ester of orthophosphoric acid having the formula $(RO)_3P=O$ wherein R is hydrogen or $C_1$ to $C_4$ alkyl, at least one R being $C_1$ to $C_4$ alkyl. The more preferred phosphorus compounds are triethylphosphate (TEP) or trimethylphosphate.

For example, VPO catalyst impregnated with triethylphosphate can be used for adding phosphorus to the VPO fluid bed catalyst and, thereby, achieving an increase in maleic anhydride yield at a lower operating temperature and significantly lower concentration of triethylphosphate relative to the amount of triethylphosphate required in the earlier vapor phase triethylphosphate addition mode.

Generally the alkyl ester of orthophosphoric acid is added to the fluid bed catalyst in an amount of about 1 to about 25 parts by weight of alkyl ester of orthophosphoric acid per 100 parts by weight of the unenriched catalyst, preferably about 7 to about 23 parts by weight of alkyl ester of orthophosphoric acid per 100 parts by weight catalyst; more preferably about 8 to about 21 parts by weight of alkyl ester of orthophosphoric acid per 100 parts by weight catalyst, and more preferably about 16 to about 19 parts by weight of alkyl ester of orthophosphoric acid per 100 parts by weight catalyst.

Attrition resistant fluid bed VPO catalysts useful for producing maleic acid or maleic anhydride from 4-carbon atom hydrocarbons, such as n-butane, n-butenes, 1,3 butadiene or a mixture thereof may be prepared as described in U.S. Pat. No. 4,647,673, incorporated herein by references in its entirety.

The catalyst may contain co-metal promoter elements. The co-metal, such as Ti, Cr, W, Ta, U, Co, Mo, Fe, Zn, Hf, Zr, Mn, As, Sb, Te, Bi, Sn, Ge, Nb, Ni, Cu, Cd, Ce, rare earths or mixtures thereof, may be added as a compound together with vanadium, or separately introduced into the solution. The co-metal promoter elements may be added to the catalyst as soluble or insoluble metals, oxides, hydroxides, carbonates, or salts such as halides, nitrates, acetates, formates, butyrates, benzylates, oxalates, and the like. These promoters may be incorporated into the catalyst precursor in any of the methods known in the art, such as inclusion via the liquid reaction medium prior to or after reduction of the vanadium, or during one or more steps of the preparation of the fluidizable catalyst.

Catalyst precursors of vanadium phosphorus mixed oxide catalysts for hydrocarbon oxidation may be prepared according to methods known in the art.

U.S. Pat. No. 4,002,650, incorporated herein by reference in its entirety, discloses the preparation of vanadium and phosphorus mixed oxide containing catalysts by reacting vanadium and phosphorus compounds in an aqueous solution, with HCl being utilized as a solvating and reducing agent for vanadium. Similar preparation techniques are described in European Patent Application No. 3,431 in which the additional step of comminuting the vanadium-phosphorus precursor to a particle size of 500 to 700 microns (0.5 to 0.7 mm) is disclosed.

U.S. Pat. No. 4,043,943, incorporated herein by reference in its entirety, discloses the preparation of the catalyst precursor in a liquid organic medium, preferably anhydrous, wherein the vanadium compound is reduced and solvated by gaseous HCl followed by reaction with the phosphorus compound.

The preparation of oxidation catalysts containing the mixed oxides of vanadium and phosphorus is disclosed in U.S. Pat. No. 4,244,879, incorporated herein by reference in its entirety, wherein a vanadium compound is at least partially solubilized in an organic liquid medium capable of reducing at least a portion of the vanadium to a +4 valence state, and unsolubilized vanadium having a particle size larger than about 0.1 mm diameter is removed from the medium before addition of a phosphorus-containing compound. The preparation of such catalysts is disclosed in U.S. Pat. No. 4,333,853, incorporated herein by reference in its entirety, wherein partial reduction of a pentavalent vanadium compound is effected in the presence of a phosphorus compound in an organic liquid medium capable of reducing the vanadium.

The catalyst precursor may be recovered from the liquid reaction medium in which it was prepared (preferably an essentially anhydrous maintained organic liquid medium) by conventional methods, such as evaporation, filtration, centrifugation, decanting, and the like. Preferably, the precursor is dried by heating. Alternatively, the recovered precursor, which is still partially wet with the organic liquid, may be treated with a low boiling solvent such as petroleum ether. In another embodiment, excess preparational reaction media may be substantially removed by vacuum filtration. In yet another embodiment, excess water can be introduced into the precursor containing organic liquid reaction medium, allowing an organic layer to separate from the aqueous layer followed by recovery of the catalyst precursor by drying.

After recovery, the catalyst precursor is subjected to densification and comminution. The order in which the catalyst precursor is densified and comminuted is dependent upon the method used for accomplishing these purposes. For example, the catalyst precursor may be densified by tableting or pelleting the catalyst precursor, and thereafter crushing or grinding the densified material to prepare it for formation of the microspheroidal particles. Alternatively, the catalyst precursor may be recovered by drying or spray drying, and thereafter subjected to dry ball milling in order to both densify the precursor material and comminute the catalyst precursor to an average particle size less than about 1 micron in diameter. The steps of densifying and comminuting the catalyst precursor may be repeated such that the final fluidizable catalyst particle has a bulk density equal to or greater than about 0.75 grams per cubic centimeter, preferably greater than or equal to 1 gram per cubic centimeter.

The densified, comminuted catalyst precursor is then formed into microspheroidal fluidizable particles. Formation may be accomplished by the oil drop method, in which an aqueous solution of the catalyst precursor is dropped into a hot oil bath to cause the formation of spheroidal particles. Preferably, the microspheroidal fluidizable particles are formed by spray drying an aqueous slurry of the catalyst precursor.

The formation of fluidizable particles by crushing and screening to form a fluidizable fraction is not suitable for forming attrition resistant catalysts, as the particles easily abrade during fluid bed operation due primarily to their irregular surface texture. Catalysts formed by crushing and screening also are more prone to fracturing, for the same reason.

If spray drying is to be utilized, the catalyst precursor preferably should be uncalcined when introduced into water to form the aqueous slurry. Substantial contacting of the calcined vanadium phosphorus mixed oxide catalyst with water (at less than 100° C.) reduces the activity of the catalyst, particularly if calcined in air.

The solids content of the catalyst precursor containing aqueous slurry should be adjusted to about 25 to about 60 weight % preferably above about 40 weight %. The catalyst precursor-containing aqueous slurry is then spray dried to form uniform, microspheroidal particles having a particle size range of between about 20 to about 300 microns, generally between 20 to about 240 microns. Spray drying may be accomplished by methods known in the art.

Inert diluents or supports may be added to the fluid bed catalyst by the addition of the diluent or support before or during any of the densification, comminution, and formation of the microspheroidal fluidizable particle steps. Such inert diluents or supports may include silica, alumina, alumina silica, titania, niobia, silicon carbide, and the like.

This method of making an attrition resistant catalyst, however, does not rely solely upon the addition of attrition resistant supports to impart attrition resistance to the catalyst. The particular combination of steps of the present invention results in the formation of an attrition resistant catalyst in which the level of inert supports may be extremely low, or absent. Generally the catalysts of the present invention include at least 70% active material. The attrition resistant fluidizable catalyst which is preferred for use in the present invention contains at least 80% active material, and most preferably at least 90% active material.

The fluidizable particles prepared above are subjected to calcination under fluidization-type conditions. Fluidization conditions can be determined readily by those of skill in the art, and include the introduction of a gas stream into a catalyst containing fluid bed vessel sufficient to "raise" the catalyst bed and contact substantially all catalyst particles with the gaseous feed, maintaining isothermal temperature control. Other calcination techniques such as cascading calcination, which, similar to fluidization calcination, provide homogeneous gas contacting of the catalyst particles and relatively isothermal temperature control, may be utilized according to the present invention, to result in fluidization-type conditions sufficient to impart attrition resistance to the calcined catalyst. Fluid bed calcination is, however, preferred.

The catalyst is calcined in air or an oxygen containing gas under fluidization-type conditions at a temperature range of about 300° C. to about 450° C. The catalyst may be calcined additionally in the presence of hydrocarbon, an inert gas, steam or both. Preferably, calcination temperature is increased from about 300° C. to about 325° C. steadily to about 400° C. to about 425° C., preferably at a rate of about 0.5° C. to about 5° C. per minute. Calcination times vary depending upon method of preparation, catalyst composition and amount of catalyst, but generally calcination is conducted for a period of time greater than 1 hour.

The catalyst precursor may contain promoter elements, including but not limited to alkali metals, alkaline earth metals, Ti, Cr, W, Ta, U, Co, Mo, Fe, Zn, Hf, Zr, Mn, As, Sb, Te, Bi, Sn, Ge, Nb, Ni, Cu, Cd, Ce, rare earths or mixtures thereof. These may be incorporated into the catalyst precursor in any of the methods known in the art, such as inclusion via the liquid reaction medium prior to or after reduction of the vanadium, or during one or more steps of the preparation of the fluidizable catalyst. The promoter elements may be added to the catalyst as soluble or insoluble metals, oxides, hydroxides, carbonates, or salts such as halides, nitrates, acetates, formates, butyrates, benzylates, oxalates, and the like. These promoters may be incorporated into the catalyst precursor in any of the methods known in the art, such as inclusion via the liquid reaction medium prior to or after reduction of the vanadium, or during one or more steps of the preparation of the fluidizable catalyst. The molar ratio of promoter elements to vanadium is generally about 0.0001:1 to about 1:1, preferably about 0.001:1 to about 0.2:1.

Catalysts suitable for the production of maleic anhydride from, 4-carbon atom hydrocarbons generally have a phosphorus to vanadium ratio of about 2:1 to about 0.5:1, preferably about 0.8:1 to about 1.3:1. Most preferred is a P/V ratio of about 1:1 to about 1.25:1. These catalysts preferably exhibit an average valence for vanadium within the range of +3.5 to +4.6, preferably about +4.

The fluid bed catalyst used in the present invention may be utilized in oxidation type fluid bed reactors known in the art.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. Preferred oxygen/hydrocarbon ratios in the reactor feed are about 4 to about 20 moles of oxygen per mole of hydrocarbon.

The reaction temperature may vary widely and is dependent upon the particular hydrocarbon and catalyst employed. Generally, temperatures of about 325° C. to 500° C. are preferred, and temperatures from about 360° C. to about 460° C. are more preferred. The reaction may be conducted at atmospheric, superatmospheric or subatmospheric pressure, although operation at superatmospheric pressure is preferred. Generally, the feed contains about 0.2 to about 5.0 mole percent butane, preferably about 1.0 to about 4.0 mole percent butane, and the butane weight hourly space velocity (wwh) is about 0.005 to about 0.2 lbs butane per lb catalyst per hour, preferably about 0.01 to about 0.1 lbs butane per lb catalyst per hour.

The advantages of fluid bed hydrocarbon oxidation processes compared to fixed bed hydrocarbon oxidation processes are well known in the art, including the improvement of temperature control and heat transfer for oxidation reactions. Catalysts which are suitable for fixed bed processes, however, are not necessarily suitable for fluid bed processes. Catalysts which are suitable for fixed bed processes in which there are few attritting forces in operation may be too "soft" to withstand the attrition caused by fluid bed operation.

Attrition of the catalyst in fluid bed operations, that is, the removal of the outer layer of the catalyst particle by abrasion or the breakup or fracture of the catalyst particle is caused by impact of the fluidized particles with each other, with the walls of the fluid bed vessel, especially within the reactor cyclones which trap the fluidized catalyst particles before they escape the reactor to return the particles to the catalyst bed.

Catalysts containing vanadium and phosphorus oxides have been used in the oxidation of 4-carbon atom hydrocarbons, such as n-butane, n-butenes, 1,3 butadiene or mixtures thereof with molecular oxygen or oxygen-containing gas to produce maleic anhydride. Conventional methods of preparing these catalysts involve reducing a pentavalent vanadium compound, and combining the same with a phosphorus compound, and if desired, promoter element compounds under conditions which will provide vanadium in a valence state below +5 to form catalyst precursors capable of being converted to an oxide. The catalyst oxide precursor is then recovered and converted to active catalytic material before or after the suitable catalyst particles for either fixed bed or fluid bed are formed.

U.S. Pat. Nos. 3,888,886; 3,905,914; 3,931,046; 3,932,305 and 3,975,300, incorporated herein by reference in their entireties, disclose the testing of promoted vanadium phosphorus oxide catalysts for maleic anhydride production from butane in one inch diameter fluid bed reactors. In most instances, the catalysts were prepared by forming the catalyst precursor in aqueous media (in U.S. Pat. No. 3,975,300 the precursor was formed in a paste of a vanadium compound, a phosphorus compound and an organic reducing agent), drying and thereafter grinding and sieving the precursor to a powder of about 74 to 250 microns size. This manner of preparation, however, does not obtain the attrition resistant catalyst particles preferred for successful fluid bed operation.

Commercial fluid bed catalysts are preferably microspheroidal particles within the range of about 20 to about 300 microns in average diameter, preferably having about 80% of the particles within the range of about 30 to about 80 microns in diameter. Most preferably, about 25 to about 40% of the particles have an average diameter of less than 45 microns.

While attrition resistant catalysts are preferred, any vanadium phosphorus oxide catalyst suitable for use in a fluid bed process for producing maleic acid or maleic anhydride from 4-carbon hydrocarbons can be used in the present invention to add phosphorus to the process. The VPO catalyst is saturated with an alkyl ester of an orthophosphate, such as triethylphosphate, and then added to the fluid bed in increments to add phosphorous to the process quantitatively as needed.

It is therefore an object of the invention to provide a process of preparing attrition resistant fluid bed vanadium and phosphorus mixed oxide containing oxidation catalysts which have been enriched with an alkyl ester of an orthophosphate, such as triethylphosphate.

Another object of the invention is to provide a process for producing maleic anhydride from 4-carbon atom hydrocarbons utilizing attrition resistant fluid bed vanadium phosphorus mixed oxide catalysts, wherein phosphorus lost from the catalysts during the reaction is replaced by the addition of catalyst which has been enriched with an alkyl ester of an orthophosphate, such as triethylphosphate.

Fluid bed VPO catalysts useful for producing maleic anhydride from 4 carbon atom hydrocarbons may be activated by contacting the fluidized catalyst containing the mixed oxides of vanadium and phosphorus with oxygen and a reducing gas at least partially combustible with oxygen at elevated temperatures sufficient to cause such combustion, wherein the molar ratio of reducing gas to oxygen is greater than the stoichiometric ratio required for complete combustion of the reducing gas as described in U.S. Pat. No. 4,748,140, incorporated herein by reference in its entirety.

The catalyst may be activated prior to loading into the reactor or after being loaded in the reactor.

The present invention has the advantage of allowing precise control of the amount of phosphorus added. Using the process of the present invention, phosphorus can be added quantitatively.

Process Description

1. TEP-enriched VPO catalyst is prepared by impregnating, at room temperature, catalyst powder with triethylphosphate at concentrations in a range of about 1 to about 25 parts by weight per 100 parts by weight of the unenriched catalyst, preferably about 7 to about 23 parts by weight per 100 parts by weight of the catalyst, more preferably about 8 to about 21 parts by weight per 100 parts by weight of the catalyst, and more preferably about 16 to about 19 parts by weight per 100 parts by weight of the catalyst. While it is possible to obtain concentrations above 25 parts by weight per 100 parts by weight catalyst, the TEP-enriched VPO catalyst powder may be too wet for easy handling and processing; however if processing can be accomplished, concentrations above 25 parts by weight per 100 parts by weight catalyst can also be used.

2. TEP enriched catalyst is added in increments to the catalyst load in the fluid bed reactor. In a commercial fluid bed reactor, the catalyst is typically added through a catalyst addition pipe in the bottom of the reactor. The fluidized catalyst flow is an up flow and the TEP-catalyst added through the catalyst pipe is drawn into the up flow and commingled with the fluidized catalyst bed.

3. Among several modes of TEP-enriched catalyst addition that were examined, direct addition of the powder to the catalyst at operating conditions was found to be most effective.

4. Based on laboratory observation of the effect of temperature and time on TEP loss from the TEP-enriched catalyst powder, an assumption was made that only about 75% of the TEP released from the TEP-enriched catalyst is available to the catalyst in the pilot reactor because the TEP-enriched catalyst is added when the catalyst flow has been stopped. It is believed that the balance of available TEP is lost to the effluent stream.

The amount of TEP which is added from the TEP-enriched catalyst to improve catalyst performance can vary depending on the amount of TEP absorbed by the VPO catalyst. Regardless of the concentration of TEP in the TEP-enriched catalyst, what is important is to add sufficient TEP to improve catalyst performance. Therefore, enough TEP-impregnated catalyst needs to be added to deliver TEP in an amount sufficient to improve catalyst performance. The amount of TEP suitable for improving the VPO catalyst performance is shown in the following ranges of TEP, which are expressed as lbs TEP per 100 lbs of total catalyst bed per day from about 0.000002 to about 1.0, more preferably about 0.00002 to about 0.2 and most preferably about 0.0002 lbs to about 0.04.

Thus sufficient TEP-impregnated VPO catalyst is added to the reactor to deliver from about 0.000002 to about 1.0 lbs of TEP per 100 lbs of total catalyst bed per day, preferably 0.00002 to about 0.2 lbs of TEP per 100 lbs of total catalyst bed per day, and more preferably about 0.0002 lbs to about 0.04 lbs of TEP per 100 lbs of total catalyst bed per day.

For example, when TEP-enriched catalyst power is mixed with catalyst powder which has not been impregnated with TEP (i.e., referred to herein as TEP-free catalyst or unenriched catalyst) before adding the mixture to the reactor, the TEP-enriched catalyst powder used in the catalyst mixture, may be impregnated with greater than 25 parts by weight TEP. In that embodiment, the TEP-enriched catalyst is impregnated with an amount of TEP sufficient to provide from about 0.000002 to about 1.0 pounds of TEP per 100 pounds of total catalyst bed per day when the fluidized mixture of TEP-enriched catalyst and TEP-free catalyst is added to the reactor. The mixture of TEP-enriched catalyst and TEP-free catalyst will preferably provide about 0.00002 to about 0.2 pounds of TEP per 100 pounds of total catalyst bed per day and most preferably about 0.0002 lbs to about 0.04 pounds of TEP per 100 pounds of total catalyst bed per day when added to the reactor.

Maleic anhydride may be recovered by a number of ways well known to those skilled in the art. For example, the recovery may be by direct condensation or by absorption in suitable media and purification of the maleic anhydride.

EXAMPLES OF THE INVENTION

It is to be understood that the subject invention is not to be limited by the examples set forth herein. These have been provided merely to demonstrate operability, and the selection of catalysts, metal sources, carbon supports, concentrations, contact times, solids loadings, feedstocks, reaction conditions, and products, if any, can be determined from the total specification disclosure provided, without departing from the spirit of the invention herein disclosed and described, the scope of the invention including modifications and variations that fall within the scope of the attached claims.

Example 1 was conducted in a 1.5" fluid bed pilot plant reactor. Due to logistical limitations in the fluid bed pilot plant, it was necessary to add the enriched catalyst as an aliquot to the top of a slumped catalyst bed at the high operating temperature. Since the air/butane flow in the reactor is an upflow, we expected that some of the TEP on the TEP-enriched catalyst would escape and hence would not be available to interact with the catalyst bed. It is our estimate that about 25% of this TEP escapes when it is added to the top of the slumped catalyst bed in the pilot plant reactor. Hence, about 75% of the TEP from the TEP-enriched catalyst is available to the catalyst bed in this reaction.

In a larger commercial reactor, there are no logistical limitations for adding the TEP-enriched catalyst, and it can be added either continuously or in aliquots. Furthermore, the TEP-enriched catalyst can be introduced at the bottom of the catalyst bed in the larger commercial reactor and hence all of the TEP is available to the catalyst bed. The TEP-enriched catalyst addition can be done continuously or as one or more aliquots in one day. For example, if one wants to add 400 lbs of TEP-enriched catalyst to a fluid bed catalyst, the 400 lbs of TEP-enriched catalyst can be added continuously over a 24 hour period at a specified rate or the 400 lbs of TEP-enriched catalyst can be added in one aliquot over a short period of time say 20 minutes. Alternatively, the 400 lbs of TEP-enriched catalyst can be added in several aliquots over a period of time, such as, for example, over one or more hours, or over the duration of a day.

The ranges of lbs of TEP per 100 lbs of catalyst per day which are suitable for practicing the present invention are from about 0.000002 to about 1.0 lb TEP per 100 lbs of catalyst bed per day, preferably from about 0.00002 to about 0.2 lb TEP per 100 lbs of catalyst bed per day, more preferably from about 0.0002 to about 0.04 lb TEP per 100 lbs of catalyst bed per day.

In one embodiment of the invention, the fluidizable catalyst containing an alkyl ester of orthophosphoric acid is added in an amount sufficient to limit the net increase in operating temperature to no more than about 20° C. Preferably, the fluidizable catalyst containing an alkyl ester of orthophosphoric acid is added in an amount sufficient to limit the net increase in operating temperature to no more than about 15° C., and more preferably the fluidizable catalyst containing an alkyl ester of orthophosphoric acid is added in an amount sufficient to limit the net increase in operating temperature to no more than about 10° C.

Example 1

Addition of TEP-Enriched Catalyst

A. Addition of Triethylphosphate (TEP) to Catalyst

Two samples of TEP-enriched catalyst were prepared such that the TEP concentrations are nominally 10 and 15 wt % respectively. For the nominal 10 wt % TEP-enriched sample, 20 parts by weight triethylphosphate liquid was added to 200 parts by weight VPO catalyst. For the nominal 15 wt % TEP-enriched sample, 30 parts by weight triethylphosphate liquid was added to 200 parts by weight VPO catalyst. The catalyst powder was tumbled for a few minutes after the triethylphosphate addition to ensure uniform distribution of the triethylphosphate in the catalyst.

B. Performance Testing

The test of the effect of adding TEP-enriched catalyst was done in 1.5" pilot plant reactors, where test conditions were 30/1 air/butane ratio, 0.05 butane weight hourly space velocity (wwh), and 10 psig. Prior to the addition of the TEP-enriched catalyst, the catalyst charge was lined-out over several days without TEP addition to ensure that all excess phosphorus has been removed. Two aliquots of 4 grams of 10% TEP-enriched powder were added to the 370-gram catalyst bed over a 2-day period. TEP-enriched powder was added at reaction temperature to a slumped bed with the air/butane feed off. The powder was pneumatically transferred from a pressurized solids-addition vessel connected to a port in the reactor head. Based on our assumption that 25% of the TEP is lost without contacting the catalyst in the pilot reactor, this would correspond to an effective addition of 3 gram/day (0.81%) of total bed) of this enriched powder.

The data for maleic anhydride yield and temperature performance with phosphorus addition via TEP-impregnated VPO catalyst are shown in Table 1. The catalyst yield increased from 43.7 mol % to about 51 mol %, or about 7 mol % increase. While temperature increased on day one by 11° F. (6.1° C.), the temperature quickly declined as the effect of added phosphorus started diminishing. After 5 days on stream, the yield declined to 46.7 mol %, but was still greater than the starting yield of 43.6 mol %. This test was continued with periodical addition of TEP-enriched VPO catalyst powder for an additional 14 days. The data clearly show that the yield was maintained at 51 mol % or more for the entire period with a net increase in operating temperature of about 10° F. (about 5.6° C.) relative to the starting point.

TABLE 1

Effect of Addition of TEP-impregnated VPO Catalyst on Catalyst Performance

| Time hours | Bed Temperature °C. | MAN % Yield | Bed Temperature °F. | 10% TEP-enriched Catalyst Addition grams | 15% TEP-enriched Catalyst Addition grams |
|---|---|---|---|---|---|
| 2 | 456 | 48.5 | 853 | | |
| 75 | 449 | 44.5 | 840 | | |
| 144 | 449 | 43.6 | 840 | | |
| 148 | | | | 4 | |
| 168 | 452 | 48.1 | 846 | | |
| 172 | | | | 4 | |
| 187 | 456 | 50.8 | 853 | | |
| 215 | 450 | 49.0 | 842 | | |
| 265 | 451 | 46.9 | 844 | | |
| 309 | 448 | 45.2 | 838 | | |
| 313 | | | | | 3 |
| 339 | 454 | 48.1 | 849 | | |
| 343 | | | | | 1.5 |
| 359 | 455 | 52.2 | 851 | | |
| 363 | | | | | 1.5 |
| 381 | 454 | 52.4 | 849 | | |
| 385 | | | | | 2 |
| 408 | 456 | 52.4 | 853 | | |
| 440 | 451 | 50.8 | 844 | | |
| 458 | 454 | 49.2 | 849 | | |
| 462 | | | | | 1.5 |
| 479 | 456 | 50.3 | 853 | | |
| 483 | | | | | 3 |
| 530 | 459 | 52.5 | 858 | | |
| 534 | 452 | 53.4 | 846 | | |
| 538 | | | | | 1.5 |
| 553 | 445 | 53.7 | 833 | | |
| 557 | | | | | 1.5 |
| 577 | 446 | 52.3 | 835 | | |
| 581 | | | | | 1.5 |
| 601 | 446 | 52.8 | 835 | | |
| 605 | | | | | 2 |
| 626 | 446 | 53.2 | 835 | | |
| 630 | | | | | 1.5 |
| 654 | | | | | 1.5 |
| 674 | 455 | 51.5 | 851 | | |

Comparative Example A

Standard TEP Addition Test Procedure—Vapor Phase Triethylphosphate Added to

The test of the effect of adding TEP continuously to the reactor as a co-fed vapor in the feed gas was conducted in a 1.5" diameter fluid-bed pilot plant reactor, where test conditions were 30/1 air/butane ratio, 0.05 butane wwh, and 10 psig pressure. TEP was fed by continuously injecting an aqueous solution of 0.33 wt. % TEP in water to the reactor's air feed line at a rate of 1.8 g/hr to provide a constant vapor concentation of 20 ppm TEP in the gaseous feed to the reactor. The reactor's air feed line was pre-heated to reactor temperature to ensure complete vaporization of the co-fed aqueous TEP solution. Prior to starting the addition of 20 ppm TEP vapor to the reactor, the catalyst charge was run without TEP for 150 hours to remove excess phosphorus from the catalyst. TEP addition at 20 ppm was then commenced and was continued for approximately 200 hours to test the effect on the catalyst.

TABLE 2

Effect of Vapor Phase Addition of 20 ppm TEP on VPO Catalyst Performance

| Time on Stream (Hours) | Bed Temperature °C. | MAN % Yield | Bed Temperature °F. |
|---|---|---|---|
| 26 | 446 | 47.3 | 835 |
| 72 | 448 | 47.4 | 838 |
| 120 | 442 | 46.3 | 828 |
| 147 | 443 | 46.3 | 829 |
| 191 | 448 | 48.7 | 838 |
| 215 | 449 | 48.6 | 840 |
| 239 | 455 | 47.7 | 851 |
| 261 | 455 | 47.8 | 851 |
| 287 | 459 | 47.1 | 858 |
| 312 | 459 | 50.4 | 858 |
| 357 | 459 | 48.1 | 858 |

Table 2 shows data from Comparative Example A, in which the standard vapor phase TEP addition in the air stream of a fluid bed MAN reactor was used. The data in Table 2 show that the on stream addition of TEP in the vapor phase produced only about 3 to about 4 mol % MAN yield increase and caused a much higher temperature increase of about 30° F. (about 16.7° C.) relative to the starting point temperature.

It is clear that addition of TEP via addition of TEP-impregnated VPO catalyst is more advantageous than the prior practice of adding TEP in the vapor phase via the air stream to the MAN fluid bed reactor.

What is claimed is:

1. A fluid bed process for the production of maleic anhydride by the oxidation of a feed comprising $C_4$ hydrocarbons with molecular oxygen or an oxygen containing gas in a fluid bed reactor at a reactor temperature of about 325° C. to about 500° C. in the presence of an attrition resistant, fluidizable microspheroidal catalyst containing the mixed oxides of vanadium and phosphorus, wherein the maleic anhydride yield in said process decreases over time due to at least one of catalyst loss from the reactor or loss of phosphorus from the catalyst, wherein the catalyst is prepared by:
    (a) preparing a vanadium phosphorus mixed oxide containing catalyst precursor;
    (b) densifying the catalyst precursor;
    (c) comminuting the catalyst precursor to an average particle size less than about one micron in diameter;
    (d) forming fluidizable particles having a bulk density greater than or equal to 0.75 grams per cubic centimeter from the densified, comminuted catalyst precursor; and
    (e) calcining the fluidizable particles under fluidization-type conditions, wherein the maleic anhydride yield in said process is improved by the addition of a make-up catalyst to said fluid bed reactor, wherein said make-up catalyst contains an alkyl ester of orthophosphoric acid having the formula $(RO)_3P=O$ wherein R is hydrogen or $C_1$ to $C_4$ alkyl, at least one R being $C_1$ to $C_4$ alkyl in an amount sufficient to provide from about 0.000002 to about 1.0 pounds of alkyl ester of orthophosphoric acid per 100 pounds of total catalyst bed per day, and wherein said make-up catalyst is prepared by impregnating catalyst prepared in accordance with (a) through (e) with the alkyl ester of orthophosphoric acid.

2. The process of claim 1 wherein the alkyl ester is triethyiphosphate.

3. The process of claim 1 wherein the alkyl ester is trimethyiphosphate.

4. The process of claim 1 wherein the make-up catalyst contains an alkyl ester of orthophosphoric acid having the formula $(RO)_3P=O$ wherein R is hydrogen or $C_1$ to $C_4$ alkyl, at least one R being $C_1$ to $C_4$ alkyl in an amount sufficient to provide from about 0.00002 to about 0.2 pounds of alkyl ester of orthophosphoric acid per 100 pounds of total catalyst bed per day.

5. The process of claim 1 wherein the added catalyst contains an alkyl ester of orthophosphoric acid having the formula $(RO)_3P=O$ wherein R is hydrogen or $C_1$ to $C_4$ alkyl, at least one R being $C_1$ to $C_4$ alkyl in an amount sufficient to provide from about 0.0002 to about 0.04 pounds of alkyl ester of orthophosphoric acid per 100 pounds of total catalyst bed per day.

6. The process of claim 1 wherein the feed contains about 0.2 to about 5.0 mole percent butane and the butane weight hourly space velocity (wwh) is about 0.005 to about 0.2 lbs butane per lb catalyst per hour.

7. The process of claim 1 wherein the fluidizable catalyst additionally comprises at least one promoter element selected from the group consisting of alkali metals, alkaline earth metals, Ti, Cr, W, Ta, U, Co, Mo, Fe, Zn, Hf, Zr, Mn, As, Sb, Te, Bi, Sn, Ge, Nb, Ni, Cu, Cd, Th, Ce, rare earths or mixtures thereof.

8. The process of claim 1, wherein the reaction temperature is from about 360° C. to about 460° C.

9. The process of claim 1, wherein the make-up catalyst containing an alkyl ester of orthophosphoric acid is added in an amount sufficient to limit any net increase in operating temperature to no more than about 20° C.

10. The process of claim 1, wherein the make-up catalyst containing an alkyl ester of orthophosphoric acid is added in an amount sufficient to limit any net increase in operating temperature to no more than about 15° C.

11. The process of claim 1, wherein the make-up catalyst containing an alkyl ester of orthophosphoric acid is added in an amount sufficient to limit any net increase in operating temperature to no more than about 10° C.

12. The process of claim 1, wherein the alkyl ester of orthophosphoric acid is triethylphosphate and make-up catalyst containing triethyiphosphate is added in an amount sufficient to limit any net increase in operating temperature to no more than about 20° C.

13. A fluid bed process for the production of maleic anhydride by the oxidation of a feed comprising $C_4$ hydrocarbons with molecular oxygen or an oxygen containing gas in a fluid bed reactor at a reactor temperature of about 325° C. to about 500° C. in the presence of an attrition resistant, fluidizable microspheroidal catalyst containing the mixed oxides of vanadium and phosphorus, wherein the maleic anhydride yield in said process decreases over time due to at least one of catalyst loss from the reactor or loss of phosphorus from the catalyst, wherein the catalyst is prepared by:
(a) preparing a vanadium phosphorus mixed oxide containing catalyst precursor;
(b) densifying the catalyst precursor;
(c) comminuting the catalyst precursor to an average particle size less than about one micron in diameter;
(d) forming fluidizable particles having a bulk density greater than or equal to 0.75 grams per cubic centimeter from the densified, comminuted catalyst precursor; and
(e) calcining the fluidizable particles under fluidization-type conditions, wherein the maleic anhydride yield in said process is improved by the addition of a make-up catalyst to said fluid bed reactor, wherein said make-up catalyst contains about 1 to about 25 parts by weight of an alkyl ester of orthophosphoric acid having the formula $(RO)_3P=O$ wherein R is hydrogen or $C_1$ to $C_4$ alkyl, at least one R being $C_1$ to $C_4$ alkyl per 100 parts by weight catalyst. and wherein said make-un catalyst is prepared by impregnating catalyst prepared in accordance with (a) through (e) with the alkyl ester of orthophosphoric acid.

14. The process of claim 13 wherein the alkyl ester is triethyiphosphate.

15. The process of claim 13 wherein the alkyl ester is trimethyiphosphate.

16. The process of claim 13 wherein the feed contains about 0.2 to about 5.0 mole percent butane and the butane weight hourly space velocity (wwh) is about 0.005 to about 0.2 lbs butane per lb catalyst per hour.

17. The process of claim 13 wherein the alkyl ester is triethyiphosphate and the added catalyst contains about 7 to about 23 parts by weight of triethyiphosphate per 100 parts by weight catalyst.

18. The process of claim 13 wherein the alkyl ester is triethylphosphate and the make-up catalyst contains about 16 to about 19 parts by weight of triethylphosphate per 100 parts by weight catalyst.

19. The process of claim 13 wherein the fluidizable catalyst additionally comprises at least one promoter element selected from the group consisting of alkali metals, alkaline earth metals, Ti, Cr, W, Ta, U, Co, Mo, Fe, Zn, Hf, Zr, Mn, As, Sb, Te, Bi, Sn, Ge, Nb, Ni, Cu, Cd, Th, Ce, rare earths or mixtures thereof.

20. The process of claim 13, wherein the reaction temperature is from about 360° C. to about 460° C.

21. The process of claim 13, wherein the make-up catalyst containing about 1 to about 25 parts by weight of an alkyl ester of orthophosphoric acid per 100 parts by weight catalyst is added in an amount sufficient to limit the net increase in operating temperature to no more than about 20° C.

22. The process of claim 21 wherein the make-up catalyst contains about 1 to about 25 parts by weight of triethyiphosphate per 100 parts by weight catalyst.

23. The process of claim 22, wherein the make-up catalyst containing about 1 to about 25 parts by weight of triethyiphosphate per 100 parts by weight catalyst is added in an amount sufficient to limit the net increase in operating temperature to no more than about 15° C.

24. The process of claim 22, wherein the make-up catalyst containing about 1 to about 25 parts by weight of triethyiphosphate per 100 parts by weight catalyst is added in an amount sufficient to limit the net increase in operating temperature to no more than about 10° C.

25. An attrition resistant, fluidizable microspheroidal catalyst containing the mixed oxides of vanadium and phosphorus, wherein the catalyst is prepared by:
(a) preparing a vanadium phosphorus mixed oxide containing catalyst precursor;
(b) densifying the catalyst precursor;
(c) comminuting the catalyst precursor to an average particle size less than about one micron in diameter;
(d) forming fluidizable particles having a bulk density greater than or equal to 0.75 grams per cubic centimeter from the densified, comminuted catalyst precursor;
(e) calcining the fluidizable particles under fluidization-type conditions; and
(f) prior to addition to a fluid bed reactor, mixing the calcined fluidizable particles obtained in (e) with an alkyl ester of orthophosphoric acid having the formula $(RO)_3P=O$ wherein R is hydrogen or $C_1$ to $C_4$ alkyl, at least one R being $C_1$ to $C_4$ alkyl, to provide fluidizable catalyst containing from about 1 to about 25 parts by weight of the alkyl ester of orthophosphoric acid per 100 parts by weight catalyst.

26. The catalyst of claim 25, wherein the fluidizable catalyst obtained in (f) contains about 7 to about 23 parts by weight of an alkyl ester of orthophosphoric acid per 100 parts by weight catalyst.

27. The catalyst of claim 25, wherein the fluidizable catalyst obtained in (f) contains about 8 to about 21 parts by weight of an alkyl ester of orthophosphoric acid per 100 parts by weight catalyst.

28. The catalyst of claim 25, wherein the fluidizable catalyst obtained in (f) contains about 16 to about 19 parts by weight of an alkyl ester of orthophosphoric acid per 100 parts by weight catalyst.

29. The catalyst of claim 25 wherein the fluidizable catalyst additionally comprises at least one promoter element selected from the group consisting of alkali metals, alkaline earth metals, Ti, Cr, W, Ta, U, Co, Mo, Fe, Zn, Hf, Zr, Mn, As, Sb, Te, Bi, Sn, Ge, Nb, Ni, Cu, Cd, Th, Ce, rare earths or mixtures thereof.

30. An attrition resistant, fluidizable miscrospheroidal catalyst containing the mixed oxides of vanadium and phosphorus, wherein the catalyst is prepared by:
 (a) preparing a vanadium phosphorus mixed oxide containing catalyst precursor;
 (b) densifying the catalyst precursor;
 (c) comminuting the catalyst precursor to an average particle size less than about one micron in diameter;
 (d) forming fluidizable particles having a bulk density greater than or equal to 0.75 grams per cubic centimeter from the densified, comminuted catalyst precursor;
 (e) calcining the fluidizable particles under fluidization-type conditions; and
 (f) prior to addition to a fluid bed reactor, mixing the calcined fluidizable particles obtained in (e) with triethyiphosphate to provide fluidizable catalyst containing from about 1 to about 25 parts by weight of triethyiphosphate per 100 parts by weight catalyst.

31. The catalyst of claim 30, wherein the fluidizable catalyst obtained in (f) contains about 7 to about 23 parts by weight of triethylphosphate per 100 parts by weight catalyst.

32. The catalyst of claim 30, wherein the fluidizable catalyst obtained in (f) contains about 8 to about 21 parts by weight of triethyiphosphate per 100 parts by weight catalyst.

33. The catalyst of claim 30, wherein the fluidizable catalyst obtained in (f) contains about 16 to about 19 parts by weight of triethylphosphate per 100 parts by weight catalyst.

34. The catalyst of claim 30 wherein the fluidizable catalyst additionally comprises at least one promoter element selected from the group consisting of alkali metals, alkaline earth metals, Ti, Cr, W, Ta, U, Co, Mo, Fe, Zn, Hf, Zr, Mn, As, Sb, Te, Bi, Sn, Ge, Nb, Ni, Cu, Cd, Th, Ce, rare earths or mixtures thereof.

* * * * *